(12) United States Patent
Goutayer et al.

(10) Patent No.: US 11,026,879 B2
(45) Date of Patent: Jun. 8, 2021

(54) DISPERSION OF DROPS OF A FIRST PHASE, DISPERSED IN A SECOND PHASE SUBSTANTIALLY IMMISCIBLE WITH THE FIRST PHASE

(71) Applicant: CAPSUM, Marseilles (FR)

(72) Inventors: Mathieu Goutayer, Saint Malo (FR); Jerome Bibette, Paris (FR)

(73) Assignee: CAPSUM, Marseilles (FR)

( * ) Notice: Subject to any disclaimer, the term of this patent is extended or adjusted under 35 U.S.C. 154(b) by 0 days.

(21) Appl. No.: 16/384,848

(22) Filed: Apr. 15, 2019

(65) Prior Publication Data
US 2019/0240138 A1 Aug. 8, 2019

Related U.S. Application Data

(62) Division of application No. 14/003,527, filed as application No. PCT/EP2012/053917 on Mar. 7, 2012, now Pat. No. 10,300,006.

(30) Foreign Application Priority Data

Aug. 3, 2011 (FR) ..................................... 1151882
Aug. 3, 2011 (FR) ..................................... 1151885

(51) Int. Cl.
| | |
|---|---|
| A61K 8/81 | (2006.01) |
| A23P 10/30 | (2016.01) |
| A23D 7/005 | (2006.01) |
| A23D 7/02 | (2006.01) |
| A61K 8/06 | (2006.01) |
| A61K 8/11 | (2006.01) |
| A61K 8/31 | (2006.01) |
| A61K 8/891 | (2006.01) |
| A61K 8/92 | (2006.01) |
| A61Q 19/00 | (2006.01) |
| B01J 13/10 | (2006.01) |
| A61K 9/10 | (2006.01) |
| A61K 9/50 | (2006.01) |
| A61K 47/32 | (2006.01) |
| A61K 47/34 | (2017.01) |

(52) U.S. Cl.
CPC .......... *A61K 8/8147* (2013.01); *A23D 7/0053* (2013.01); *A23D 7/02* (2013.01); *A23P 10/30* (2016.08); *A61K 8/062* (2013.01); *A61K 8/11* (2013.01); *A61K 8/31* (2013.01); *A61K 8/891* (2013.01); *A61K 8/922* (2013.01); *A61K 9/10* (2013.01); *A61K 9/5026* (2013.01); *A61K 47/32* (2013.01); *A61Q 19/00* (2013.01); *B01J 13/10* (2013.01); *A61K 47/34* (2013.01); *A61K 2800/412* (2013.01)

(58) Field of Classification Search
USPC ........................................................ 514/772.6
See application file for complete search history.

(56) References Cited

U.S. PATENT DOCUMENTS

| | | | |
|---|---|---|---|
| 6,534,091 B1 | 3/2003 | Garces | |
| 2004/0166165 A1* | 8/2004 | Mistry | B01J 13/08 |
| | | | 424/490 |
| 2007/0196400 A1 | 8/2007 | Raschke et al. | |
| 2012/0003285 A1 | 1/2012 | Bibette et al. | |

FOREIGN PATENT DOCUMENTS

| | | |
|---|---|---|
| CN | 101 612 139 | 12/2009 |
| DE | 10 2008 002145 | 12/2009 |
| EP | 1 524 030 | 4/2005 |
| FR | 2 939 012 | 6/2010 |
| GB | 2 135 954 | 9/1984 |
| WO | 03/002248 | 1/2003 |

OTHER PUBLICATIONS

F. Weinbreck et al. (Microencapsulation of oilsusing whey protein/gum arabic coacervates, Journal of Microencapsulation, 2004,21:6, 667-679).*
H. Träubel, New Materials Permeable to Water Vapor Springer-Verlag Berlin Heidelberg 1999, chapter 18—hydrophillic Polymers, pp. 133-152.*
S. Wen, et al.; "Microcapsules through polymer complexation—Part 3: Encapsulation and Culture of Human Burkitt Lymphoma Cells in Vitro"; Biomaterialsm Elsevier Science Publishers BV. Barking GB, vol. 16, No. 4, Jan. 1, 1995; pp. 325-335; XP004033057; pp. 325-335.
The definition of "including", Merriam-Webster [online] [retrieved on Nov. 27, 2015], Retrieved from :http://www.merriam-webster.com/dictionary/include.

\* cited by examiner

*Primary Examiner* — Johann R Richter
*Assistant Examiner* — Courtney A Brown
(74) *Attorney, Agent, or Firm* — Nixon & Vanderhye

(57) ABSTRACT

The invention deals with a dispersion of drops of a first phase in a second phase substantially immiscible with the first phase, the solubility of the first phase in the second phase being less than 5% by mass. Each drop includes a core formed with a first phase and a shell formed with a coacervate layer interposed between the first phase and the second phase.
The coacervate layer comprises a first precursor polymer of the coacervate and a second precursor polymer of the coacervate, one of the first phase and of the second phase is aqueous, and the other of the first phase and of the second phase is oily.

18 Claims, 4 Drawing Sheets

US 11,026,879 B2

DISPERSION OF DROPS OF A FIRST PHASE, DISPERSED IN A SECOND PHASE SUBSTANTIALLY IMMISCIBLE WITH THE FIRST PHASE

CROSS-REFERENCE TO RELATED APPLICATIONS

This application is a divisional of U.S. Ser. No. 14/003,527 filed Oct. 30, 2013, which was a national stage application, filed under 35 U.S.C. § 371, of International Patent Application No. PCT/EP2012/053917 filed Mar. 7, 2012, which claims priority to FR application No. 1151882 filed Aug. 3, 2011 and FR 1151885 filed Aug. 3, 2011.

BACKGROUND OF THE INVENTION

Field of the Invention

The present invention relates to a method for forming drops of a first phase, dispersed in a second phase substantially immiscible with the first phase, each drop including a core formed with first phase and a shell formed with a coacervate layer interposed between the first and the second phase, the method comprising the following steps:
providing a first fluid comprising the first phase and a first precursor polymer of the coacervate contained in the first phase;
forming first fluid drops in a second fluid intended to form the second phase.

Such a method is for example intended to form a dispersion of the water-in-oil type comprising stable drops of dispersed phase, with a size greater than 500 microns, and notably comprised between 500 microns and 2,500 microns, preferably between 700 microns and 1,500 microns. Alternatively, the dispersion is of the oil-in-water type.

The dispersed phase is intended to contain for example a cosmetic product, a biologically active product, or an edible product capable of being consumed.

Description of Related Art

From WO 03/002248, a method of the aforementioned type is known, intended to disperse a detergent in an oily phase in the form of drops. The shell of the drops is formed by a coacervate of polymers.

In this respect, a first precursor of the coacervate, formed by melamine, is mixed with a second precursor of the coacervate, formed by formaldehyde. These polymers are placed in an aqueous solution containing the detergent. A coacervation catalyst, formed by citric acid, is also added into the aqueous phase.

This aqueous phase is then dispersed in an oily solvent in the presence of an amphipathic stabilization polymer.

Next, the dispersion is heated to a relatively high temperature in order to cause the formation of coacervate at the interphase, by phase separation and polymerization.

Such a method does not give entire satisfaction. Indeed, although the presence of the stabilizer in the oily phase limits the formation of gel in this phase, the presence of the coacervation precursors in the aqueous phase does not guarantee their adequate placement at the interphase between the aqueous phase and the oily phase, when polymerization is started.

Subsequently, the formed shell does not always ensure satisfactory retention of the dispersed phase and may sometimes have a large thickness.

BRIEF SUMMARY OF THE INVENTION

An object of the invention is to have available a method for forming a plurality of drops of a first phase, dispersed in a second phase, with which it is possible to obtain highly stable drops, stabilized with a very thin shell.

Another object of the invention is to obtain a method for making a stable dispersion of drops of first phase in second phase which may be highly concentrated, while remaining capable of flowing, notably at low shears.

For this purpose, the object of the invention is a method of the aforementioned type, characterized in that it comprises the following steps:
introducing a second precursor polymer of the coacervate into the second fluid;
during the formation of each drop, or once each drop is formed, generating the coacervate layer by interaction between the first precursor polymer and the second precursor polymer at the interface between the first phase and the second phase.

The method according to the invention may comprise one or more of the following features, taken individually or according to any technically possible combination:
the step of forming drops comprises the formation of drops of a first fluid at the outlet of a first conduit opening into the second fluid;
the second phase is circulated in a second conduit, the outlet of the first conduit opening into the second conduit, advantageously coaxially with the local axis of the second conduit;
the second conduit opens downstream into a receptacle while being immersed in a liquid received in the receptacle;
the drops of a first phase have a diameter of more than 500 microns, advantageously less than 3,000 microns, notably comprised between 800 microns and 2,000 microns;
introducing the second precursor polymer into the second fluid is carried out after forming said or each drop, advantageously in a reaction fluid miscible with the second fluid;
the method comprises the introduction into the second fluid of a reaction agent capable of generating the interaction between the first precursor polymer and the second precursor polymer in order to form the shell after the formation of each drop;
the interaction between the first precursor polymer of the coacervate and the second precursor polymer of the coacervate in order to form the shell is an ionic interaction;
the first precursor of the coacervate is a first polymer which may be ionized in order to have a first charge, the second precursor of the coacervate being a second polymer which may be ionized in order to have a second charge opposite to the first charge;
one of the first precursor and the second precursor is a lipophilic polymer which may be ionized in contact with an aqueous phase, for example a polymer containing a silicone and containing a functional group which may be ionized, the lipophilic polymer being advantageously a derivative of dimethicone, such as amodimethicone, copolymers of acrylate and dimethicone and derivatives thereof;
the lipophilic polymer is a cationic lipophilic polymer such as a polymer having a primary, secondary or tertiary amine function, or such as a silicone polymer having amine functions, polylysine or polyetherimine or is further an anionic lipophilic polymer such as a polymer or copolymer having a carboxylic acid function such as polyacrylic acid, or having an acrylic acid function, a methacrylic acid function, a crotonic acid function, or a maleic acid function;

the other of the first precursor polymer and the second precursor polymer is a hydrophilic polymer which may be ionized;

the other of the first precursor and the second precursor is an acrylic hydrophilic polymer such as a copolymer of acrylic acid or maleic acid and of at least one other monomer, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypolyethyleneglycol methacrylates, hydroxyester acrylates;

the other of the first precursor and the second precursor is selected from a cationic hydrophilic polymer such as chitosan or derivatives of guar gum, notably guar hydroxypropyltrimonium chloride;

the first phase is aqueous and the second phase is oily;

the first phase is oily and the second phase is aqueous;

the step of forming drops includes the introduction of a continuous volume of a first fluid and of a continuous volume of a second fluid, and then the stirring of the first fluid and of the second fluid in order to form a dispersion of the first phase in the second phase;

the step of introducing the second precursor polymer includes the addition of a fluid containing the second precursor polymer in the second fluid, and the stirring of this fluid containing the second precursor polymer in order to disperse it into the second phase containing the first phase drops;

the shell has a thickness of less than 1 μm, notably less than 100 nm, advantageously less than 50 nm, in particular less than 10 nm;

the shell has a thickness comprised between 1 nm and 500 nm;

it includes the forming of a film of an intermediate fluid miscible with the first fluid around each drop of first fluid in the second fluid, and then the mixing between the film of intermediate fluid and the first fluid in order to put the first precursor polymer of the coacervate in contact with the second precursor polymer of the coacervate.

Another object of the invention is a dispersion of drops of a first phase in a second phase substantially immiscible with the first phase, notably which may be obtained by a method as defined above.

The dispersion according to the invention may comprise one or more of the following features:

the drops have a diameter of more than 500 micrometers and advantageously less than 3,000 microns, notably comprised between 800 microns and 2,000 microns, each drop including a core formed by a first phase and a shell formed by a coacervate layer interposed between the first phase and the second phase, the shell having a thickness of less than 1,000 nanometers, notably comprised between 1 nanometer and 500 nanometers;

the coacervate layer comprises a first precursor polymer of the coacervate and a second precursor polymer of the coacervate, the first precursor polymer of the coacervate being a first polymer which may be ionized in order to have a first charge, the second precursor polymer of the coacervate being a second polymer which may be ionized so as to have a second charge opposite to the first charge;

one of the first phase and the second phase is aqueous, and the other one of the first phase and of the second phase is oily;

a perfuming agent is placed in one of the first phase and the second phase, advantageously in an oily phase;

the first phase comprises a population of monodispersed drops having average diameters comprised between 500 micrometers and 3,000 micrometers;

the coefficient of variation of the diameters of the drops of the dispersion is less than or equal to 10%;

each drop comprises, by mass based on the mass of the drop:
from 0.05% to 10% of a polymer P1 of the anionic and hydrophilic type, and
from 0.05% to 10% of a polymer P2 of the cationic and lipophilic type;

each drop comprises, by mass based on the mass of the drop:
from 0.05% to 10% of a polymer P1 of the cationic and hydrophilic type, and
from 0.05% to 10% of a polymer P2 of the anionic and lipophilic type;

each drop comprises, by mass based on the mass of said drop:
from 0.05% to 10% of a polymer P1 of the anionic and hydrophilic type, and
from 0.05% to 10% of a polymer P1' of the cationic and hydrophilic type;

the first phase represents at least 60% by volume based on the total volume of the dispersion;

one of the first phase and the second phase is an oily phase comprising one or several oils selected from the group comprising silicone oils, mineral oils, vegetable oils, fatty acid and/or fatty alcohol esters, typically $C_1$-$C_{20}$ esters and oils compatible with the esters such as apolar solvents;

the dispersion is substantially translucent;

the drops of the dispersion are substantially non-elastic;

the shear modulus of the dispersion, under shearing equal to 2 $s^{-1}$, is less than 200 Pa·s and notably less than 100 Pa·s;

the dispersion includes a perfuming agent, the mass content of perfuming agent in the dispersion being comprised between 1% by mass and 60% by mass, advantageously between 5% by mass and 40% by mass;

the second phase is oily, the perfuming agent being contained in the second phase;

the first phase is oily, the perfuming agent being comprised in the first phase;

the dispersion is without any surfactant, notably without any anionic surfactant.

The invention also relates to a cosmetic composition comprising a dispersion as defined above.

Another object of the invention is the use of the dispersion as defined above for preparing a cosmetic composition, and the use of the dispersion according to the invention as a cosmetic composition.

BRIEF DESCRIPTION OF THE SEVERAL VIEWS OF THE DRAWINGS

The invention will be better understood upon reading the description which follows, only given as an example, and made with reference to the appended drawings, wherein.

DETAILED DESCRIPTION OF THE INVENTION

FIGS. 1 to 4 illustrate the application of a first method for forming drops according to the invention.

Figure 1:
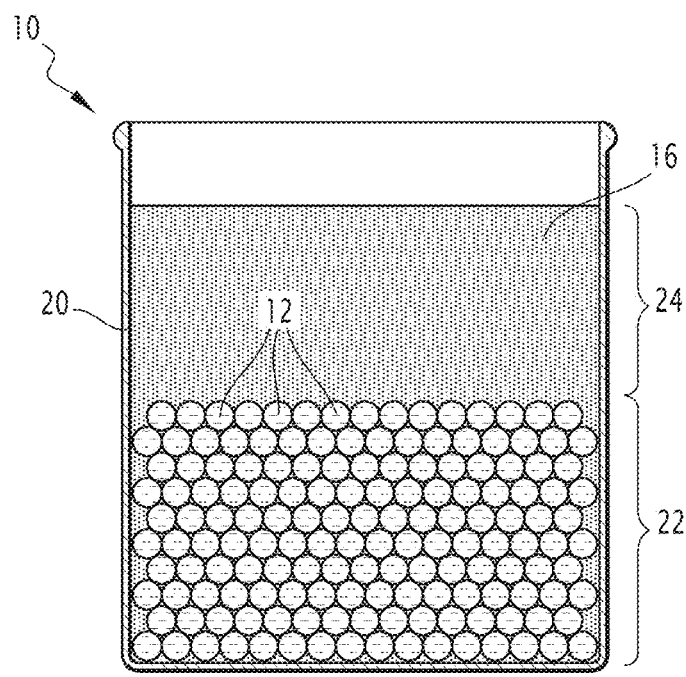
FIG. 1 is a schematic side view of a first dispersion according to the invention, contained in a container.

With reference to FIG. 1, this first method is intended to form a dispersion 10 of drops 12 of a first phase 14 dispersed in a second phase 16 substantially immiscible with the first phase 14.

In this example, the first phase 14 is for example an aqueous phase. It notably contains in liquid form, a first product which is selected from a biologically active product, a cosmetic product or an edible product capable of being consumed.

When the first product is a biologically active product, it is advantageously selected from anticoagulants, anti-thrombogenic agents, anti-mitotic agents, anti-proliferation, anti-adhesion, anti-migration agents, cell adhesion promoters, growth factors, anti-parasite molecules, anti-inflammatory agents, angiogenic agents, inhibitors of angiogenesis, vitamins, hormones, proteins, anti-fungal agents, anti-microbial molecules, antiseptics or antibiotics.

Alternatively, the first phase 14 contains reactive agents such as proteins or reagents intended to form a bioreactor, or to form artificial cells for implants.

A cosmetic product which may be obtained in the core is for example mentioned in the Council Directive 93/35/EEC as of Jun. 14, 1993. This product is for example a cream, an emulsion, a lotion, a gel or an oil for skin (hands, face, feet, etc.), a foundation (liquid, slurry), a preparation for baths and showers (salts, foams, oils, gels, etc.), a hair care product (hair dyes and bleaches), a cleaning product (lotions, powders, shampoos), a hair maintenance product (lotions, creams, oils), a hair styling product (lotions, lacquers, hair shine products), a shaving product (soaps, foams, lotions, etc.), a product intended to be applied on lips, a sunscreen product, a sunless tanning product, a skin whitening product, an anti-wrinkle product.

The edible products which may be consumed by a human being or by an animal advantageously are vegetable or fruit purees such as mango puree, pear puree, coconut puree, cream of onions, of leeks, of carrots, or other preparations which may mix several pieces of fruit or vegetables. Alternatively, these are oils such as food oil, of the olive oil, soya bean oil, grape oil, sunflower oil type or any other oil extracted from plants.

The second phase 16 is advantageously an oil. This phase is made for example from liquid oil with a viscosity of less than 20,000 mPa·s, preferably bellow a 1,000 mPa·s.

The oil making up the oily phase is for example a silicone oil, a mineral oil, a vegetable oil or a mixture of these oils.

The second oily phase 16 comprises, in one alternative, molecules of cosmetic interest, such as active agents, coloring agents, stabilizers, preservatives, modifying agents selected from texture agents, viscosity agents, pH agents, osmotic force agents or refractive index modifiers.

Advantageously, the dispersion 10 is substantially translucent.

By substantially translucent, is meant that the absorbance of the dispersion according to the invention is generally less than 5%, preferably less than 2%, preferentially less than 1% for at least one wavelength in the visible spectrum comprised between 400 nanometers and 1,000 nanometers, advantageously over any wavelength of the visible spectrum from 400 nanometers to 1,000 nanometers.

The intensity transmitted through the dispersion 10 according to the invention is divided by a factor of at least $10^3$ as compared with a conventional concentrated emission.

This translucence is measured by introducing a dispersion sample in a bowl with an optical path of 2 mm at a wavelength comprised between 400 nanometers and 1,000 nanometers.

The first phase 14 and the second phase 16 are substantially immiscible. Thus, the solubility of the first phase 14 in the second phase 16 is advantageously less than 5% by mass.

Figure 2:
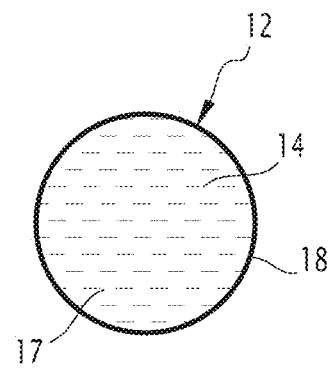
FIG. 2 is an enlarged view of a drop of first phase contained in the second phase and having a coacervate shell, the drop having been obtained by a first method according to the invention.

With the method according to the invention, it is possible to obtain a plurality of drops 12 of a first phase 14 as illustrated in FIG. 2. Each drop 12 thus includes a core 17 composed of the first phase 14 and a shell 18 for retaining and stabilizing the core 17, the shell 18 being formed by a coacervate between a first precursor polymer and a second precursor polymer, as described in detail below.

In the example illustrated in FIG. 1, each drop 12 has a density greater than that of the second phase 16 in which it is dispersed.

Thus, the drops 12 accumulate at the bottom of the container 20 which receives the dispersion 10. The drops 12 are positioned while bearing upon each other. Subsequently, the dispersion comprises at least one concentrated region 22 including drops 12 and at least one region 24 without any drop 12 and exclusively comprising some second phase 16.

In the example illustrated in FIG. 1, the concentration of drops in the concentrated region 22 is high, so that the volume content of the first phase in the concentrated region 22 is more than 50% and is notably more than 60%.

In this example, the diameter of the drops 12 is more than 500 μm, and is advantageously less than 3,000 μm.

Advantageously, the diameter of the drops is comprised between 500 microns and 2,500 microns. The drops 12 are visible in the aqueous phase 16.

In an embodiment, when the drops of the dispersion have a size of more than 500 μm, the invention offers to provide a dispersion of the water-in-oil type, the drops 12 of which have a uniform size distribution.

More specifically, according to this embodiment, the dispersed aqueous phase consists in a population of monodispersed drops such that they have an average diameter $\overline{D}$ comprised between 500 μm and 3 000 μm and a variation coefficient $C_v$ of less than 10%.

Within the scope of the present description, by «monodispersed drops» is meant that the population of dispersed drops of the dispersion according to the invention has a uniform size distribution. Monodispersed drops have good monodispersity. Conversely, drops having poor monodispersity are said to be «polydispersed».

The average diameter $\overline{D}$ of the drops is for example measured by analyzing a photograph of a batch consisting in N drops, with an image processing software package (Image J). Typically, according to this method, the diameter is measured in pixels, and then referred to in µm, depending on the size of the container containing the drops of the dispersion.

Preferably, the value of N is selected to be greater than or equal to 30, so that this analysis reflects in a statistically significant way the distribution of diameters of the drops of said emulsion.

The diameter $D_i$ of each drop is measured and then the average diameter $\overline{D}$ is obtained by calculating the arithmetic mean of these values $D_i$:

$$\overline{D} = \frac{1}{N}\sum_{i=1}^{N} D_i$$

From these values $D_i$, it is also possible to obtain the standard deviation σ of the diameters of the drops of the dispersion:

$$\sigma = \sqrt{\frac{\sum_{i=1}^{N}(D_i - \overline{D})^2}{N}}$$

The standard deviation σ of a dispersion reflects the distribution of the diameters $D_i$ of the drops of the dispersion around the average diameter $\overline{D}$.

By knowing the average diameter $\overline{D}$ and the standard deviation σ of a dispersion, it is possible to determine that 95% of the population of drops is found in the interval of diameters $[\overline{D}-2\sigma;\overline{D}+2\sigma]$ and that 68% of the population is found in the interval $[\overline{D}-\sigma;\overline{D}+\sigma]$.

In order to characterize the monodispersity of the dispersion according to this embodiment of the invention, the variation coefficient $C_v$ may be calculated:

$$C_v = \frac{\sigma}{\overline{D}}$$

This parameter reflects the distribution of the diameters of the drops versus the average diameter of the latter.

The variation coefficient of the diameters of the drops of the dispersion according to this embodiment of the invention is less than 10%, preferably less than 5%.

Alternatively, the monodispersity may be demonstrated by placing a dispersion sample 10 in a flask with a constant circular section. Mild stirring by rotating by one quarter turn over one half of a second around the axis of symmetry crossing the flask, followed by resting for half of a second, is carried out, before repeating the operation in the opposite direction, and this four times in a row.

The drops 12 of the dispersion organize in crystalline form when they are monodispersed drops. Thus, they have a stack according to a pattern successively being repeated in the three dimensions. It is then possible to observe a regular stack which indicates good monodispersity, an irregular stack expressing polydispersity of the dispersion.

When the dispersion is left at rest, the drops 12 are stable and do not adhere to each other, no coalescence is observed after 2 weeks at 40° C.

The dispersion according to the invention supports shear-free stirring without being subject to significant coalescence of the drops 12 or to an alteration of its monodispersity.

In order to test this properly, a sample of the dispersion according to the invention is placed in a 2 mL container, and then the latter is placed in a cell of a stirring tray (IKA vortex Genius 3). The size of a cell is about 50% greater than that of the container containing the sample. Thus, during stirring, the container strikes the walls of the cell, which generates a large number of impacts. The stirring rate is about 500 rpm. The test is considered as being successful when less than 5% of the drops by number have been subject to coalescence after one hour of stirring without any shear.

In addition to the properties mentioned above, such drops are non-elastic, and have a granular behavior when the dispersion is stirred, so that they flow on each other like solid objects and they adopt a particulate behavior in suspension.

Further, the dispersion according to the invention may have the following properties.

According to certain advantageous embodiments, the dispersion according to the invention tolerates falling from a height of one meter without being subject to substantial coalescence of the drops, or to an alteration of its monodispersity.

In order to test this property, a sample of the dispersion according to the invention is placed in a 2 mL container, and then the latter is released at the top of a glass tube from a height of one meter, used as a guide, on a solid substrate and recovered at its lower end. The operation is repeated three times. The test is considered as being successful when less than 5% of drops 12 by number have been subject to coalescence at the end of the three falls.

The drops 12 are substantially non-elastic. The non-elasticity of the drops may be characterized by a very low flow resistance threshold, for example measured by the following method: a dispersion sample 10 is placed in a rheometer of the rheometrics RFSII type using a cone-plane geometry having a gap of 45 micrometers. The investigated shears are low, and are notably comprised between 1 $s^{-1}$ and 10 $s^{-1}$. The shear modulus is noted for increasing shears between 1 $s^{-1}$ and 10 $s^{-1}$.

Thus, the shear modulus, under low shearing, notably equal to 2 $s^{-1}$, is less than 200 Pa·s, and is notably less than 100 Pa·s.

This shear modulus is less by at least $10^4$ than the shear modulus observed at the same shear, for a conventional dispersion stabilized with surfactants and having the same oil and water composition.

As compared with a conventional monodispersed emulsion (oil/water) at a concentration of 80% (cf. Mason et al. J. Coll. Int. Sci. 179, 439-448 (1996)), a concentrated emulsion according to this embodiment has a viscosity η (Pa·s) less by a factor $10^4$, for shearing ranging from 1 to 12 $s^{-1}$.

The core 17, even surrounded with the shell 18, is substantially liquid or not very gelled. Alternatively, the core is gelled.

By means of the method according to the invention, the drops 12 obtained by this method have a very thin shell 18, notably with a thickness of less than 1% of the diameter of the drops 12.

The thickness of the shell 18 is thus less than 1 µm and is too small for being measured with optical methods. This size is generally comprised between 1 nm and 500 nm, preferably less than 100 nm, advantageously less than 50 nm, preferentially less than 10 nm.

The measurement of the thickness of the shell of the drops of the invention may be carried out by a small angle neutron scattering method (Small-Angle X-ray Scattering), as applied in Sato et al. J. Chem. Phys. 111, 1393-1401 (2007).

For this, the drops are produced by using deuterated water, then washed three times with deuterated oil, such as for example a deuterated oil of the hydrocarbon type (octane, dodecane, hexadecane).

After washing, the drops are then transferred into the neutron cell in order to determine the spectrum $1(q)$; q being the wave vector.

From this spectrum, conventional analytic treatments (REF) are applied in order to determine the thickness of the hydrogenated (non-deuterated) shell.

The shell 18 surrounding the drops of the emulsion according to the invention is stiffened, which has the advantage of giving greater strength to the drops and of reducing, or even preventing their coalescence.

This shell is typically formed by coacervation, i.e. by precipitation of charged polymers with opposite charges. Within a coacervate, the bonds binding the charged polymers together are of the ionic type and are generally stronger than bonds of the electrostatic type present within a membrane of the surfactant type.

The shell 18 is formed by coacervation of at least two charged polymers with opposite polarities (or polyelectrolyte) and preferably in the presence of a first polymer of the anionic type and of a second polymer, different from the first polymer, of the cationic type.

Within the scope of the present description, by «polymer of the anionic type» is meant a polymer including chemical functions of the anionic type. This may also be referred to as an anionic polyelectrolyte.

By «chemical function of the anionic type», is meant a chemical function AH capable of yielding a proton in order to obtain a function $A^-$. Depending on the conditions of the medium in which it is found, the polymer of the anionic type therefore includes chemical functions in the AH form, or else in the form of its conjugate base $A^-$.

As example of chemical functions of the anionic type, mention may be made of carboxylic acid functions —COOH, optionally present in the form of a carboxylate anion —COO$^-$.

As an example of a polymer of the anionic type, mention may be made of any polymer formed by the polymerization of monomers, at least one portion of which bears chemical functions of the anionic type, such as carboxylic acid functions. Such monomers are for example acrylic acid, maleic acid or any ethylenically unsaturated monomer including at least one carboxylic acid function.

Among the examples of a polymer of the anionic type, suitable for applying the invention, mention may be made of copolymers of acrylic acid or maleic acid and of other monomers, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypolyethyleneglycol methacrylates, hydroxy ester acrylates.

Within the scope of the present invention, by «polymer of the cationic type» is meant a polymer including chemical functions of the cationic type. This may also be referred to as a cationic polyelectrolyte.

By «chemical function of the cationic type», is meant a chemical function B capable of capturing a proton in order to obtain a function $BH^+$. Depending on the conditions of the medium in which it is found, the polymer of the cationic type therefore includes chemical functions in the B form, or else in the $BH^+$ form, its conjugate acid.

As an example of chemical functions of the cationic type, mention may be made of primary, secondary and tertiary amine functions, optionally present in the form of ammonium cations.

As an example of polymer of the cationic type, mention may be made of any polymer formed by the polymerization of monomers, at least one portion of which bearing chemical functions of the cationic type, such as primary, secondary or tertiary amine functions.

Such monomers are for example aziridine, or any ethylenically unsaturated monomer including at least one primary, secondary or tertiary amine function.

Among the examples of a polymer of the cationic type, suitable for applying the invention, mention may be made of amodimethicone, derived from a silicone polymer (polydimethylsiloxane, also called dimethicone), modified with primary amine and secondary amine functions:

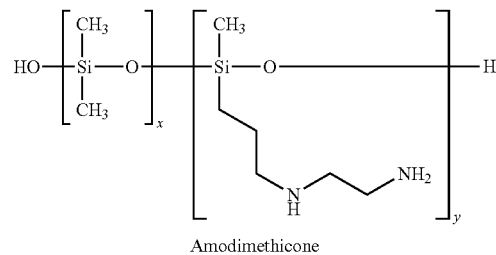

Amodimethicone

Mention may also be made of derivatives of amodimethicone, such as for example copolymers of amodimethicone, aminopropyl dimethicone and more generally silicone polymers including amine functions.

Mention may be made of the copolymer of bis-isobutyl PEG-14/amodimethicone and bis-hydroxy/methoxy amodimethicone.

Mention may also be made of polymers of the polysaccharide type comprising amine functions, such as chitosan or guar gum derivatives (guar hydroxpropyletrimonium chloride).

Mention may also be made of polymers of the polypeptide type comprising amine functions such as polylysine.

Mention may also be made of polymers of the polyethyleneimine type comprising amine functions such as linear or branched polyethyleneimine.

Coacervation generally takes place in the presence of a first polymer of the anionic type and of a second polymer of the cationic type, which play the role of agents for stiffening the membrane.

The formation of the coacervate between these two polymers is generally caused by a modification of the conditions of the reaction medium (temperature, pH, concentration of reagents, etc.). The coacervation reaction results from the neutralization of these two charged polymers with opposite polarities and allows the formation of a membrane structure by electrostatic interactions between the first and the second polymer. The thereby formed membrane around each drop totally encapsulates the core 17 and isolates the first phase 14 from the second phase 16.

As this will be seen below in the description of the method according to the invention, the first polymer is initially contained in one of the first phase 14 and the second phase 16, the second polymer being initially contained, before formation of the drops 12, in the other of the first phase 14 and the second phase 16. Both polymers then migrate to the interface during the formation of the drops where they form the shell 18 by coacervation.

An advantageous dispersion is such that each drop comprises, by mass based on the mass of said drop:
- from 0.05% to 10% of a polymer $P_1$ of the anionic and hydrophilic type, and
- from 0.05% to 10% of a polymer $P_2$ of the cationic and lipophilic type.

Preferably, each drop comprises, by mass based on the mass of said drop, from 0.1% to 5% of a polymer $P_1$ of the anionic and hydrophilic type.

Preferably, each drop comprises, by mass based on the mass of said drop, from 0.1% to 5% of a polymer $P_2$ of the cationic and lipophilic type.

An advantageous dispersion according to this alternative is that each drop comprises a polymer $P_1$ of the anionic and hydrophilic type, and a polymer $P_2$ of the cationic and lipophilic type, in a mass ratio $P_1:P_2$ comprised between 1:10 and 10:1.

Figure 3:
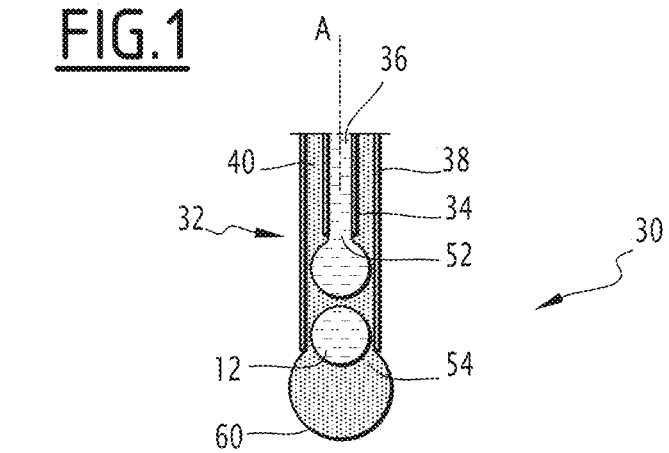
FIG. 3 is a schematic side view of a first apparatus for applying the method according to the invention, during the application of this method.
Figure 3:
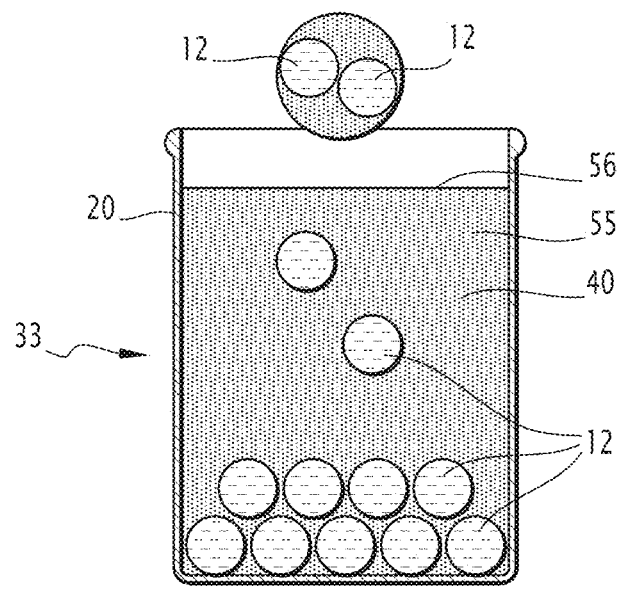
Figure 4:
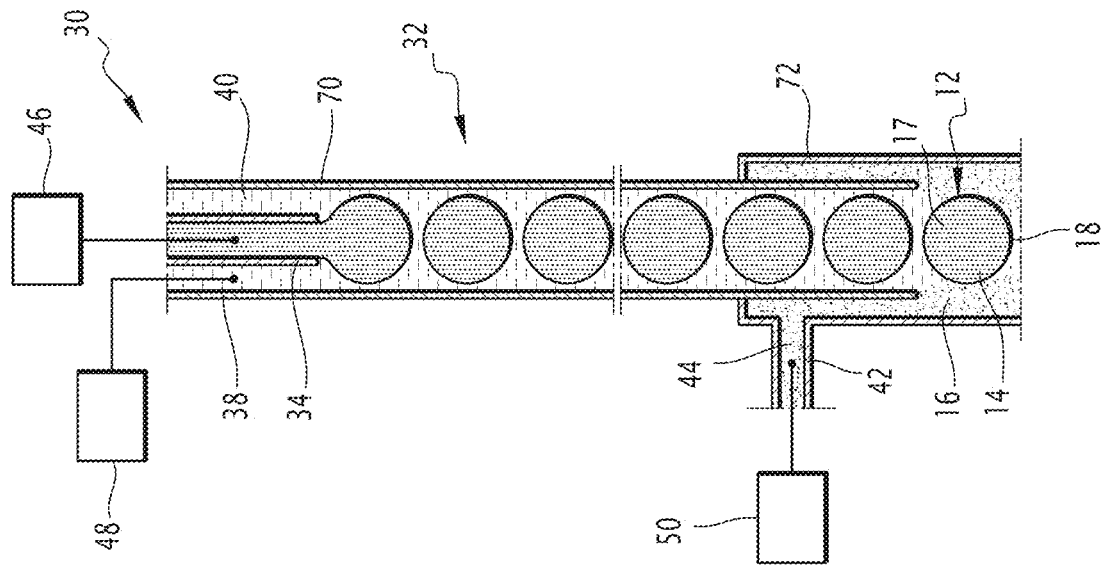
FIG. 4 is an enlarged view of the nozzle for forming drops, of the first device according to the invention.

The first method according to the invention is applied by means of a microfluidic method in an apparatus 30 illustrated by FIGS. 3 and 4.

This apparatus 30 includes a nozzle 32 for forming drops and a receptacle 33 for receiving the drops formed.

The formation nozzle 32 includes an internal conduit 34 for introducing an internal fluid 36 comprising the first phase 14, and an external conduit 38 arranged around the internal conduit 36 for introducing an external fluid 40 forming at least one portion of the second phase 16.

Figure 5:
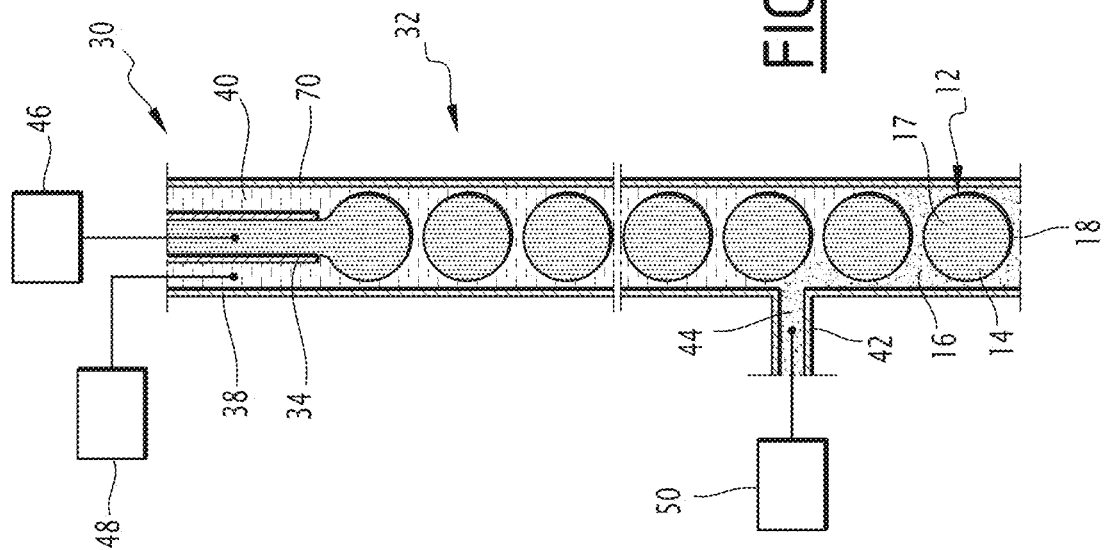
FIG. 5 is a view similar to FIG. 4 of an alternative nozzle.

In the example illustrated by FIGS. 4 and 5, the nozzle 32 further comprises advantageously a conduit 42 for introducing a reaction fluid 44, opening into the external conduit 36.

The apparatus 30 further includes means 46 for introducing an internal fluid 36 into the internal conduit 34, means 48 for introducing an external fluid 40 into the annular space delimited between the internal conduit 34 and the external conduit 38 and means 50 for introducing a reaction fluid 44 into the conduit 42 for introducing a reaction fluid when the latter is present.

In the example illustrated in FIGS. 3 and 4, the maximum diameter of the conduits 34, 38 and 42 is less than 3 mm in order to preserve the microfluidic nature of the method.

The internal conduit 34 is advantageously arranged coaxially in the external conduit 38. It is connected upstream to the introduction means 46. It opens downstream through a downstream opening 52 arranged in the external conduit 38, set back relatively to the downstream opening 54 defined by the external conduit 38, above this opening 54.

Thus, the distance separating the downstream opening 52 of the internal conduit 34 and the downstream opening 54 of the external conduit 38 is preferably greater than once the diameter of the external conduit 38.

The external conduit 38 delimits with the internal conduit 34 an annular space connected upstream to the introduction means 48.

The downstream opening 54 of the external conduit 38 is located above and away from the container 33. It thus opens into an air space.

The introduction conduit 42 transversely opens into the external conduit 38, downstream from the downstream opening 52 of the internal conduit 36 and upstream from the downstream opening 54 of the external conduit 38. It is connected upstream to the introduction means 50.

The introduction means 46, 48 and 50 each for example include a syringe pump, a peristaltic pump or another pressure generating system controlling the flow rate, such as for example a pressure pot coupled with a flow meter and a flow rate control system.

Each of the introduction means 46, 48, 50 is able to convey a respective fluid 36, 40, 44 at a controlled and adjusted flow rate.

The container 33 is placed above the downstream opening 54. It contains a volume 55 of liquid intended to form another portion of the second phase 16, advantageously an external fluid volume 40.

The upper surface of the fluid volume 55 is located axially away from the downstream opening 54, taken along the axis A-A', so that the drops 12 formed in the nozzle 32 fall under the effect of their weight through an air space between the downstream opening 54 and the upper surface 56 of the volume 55 of liquid.

In an alternative (not shown), the downstream opening 54 is immersed in the volume of fluid 55.

In the example illustrated in FIG. 3, the device 30 has been illustrated with a single nozzle 32.

In an advantageous alternative, the system 30 includes a plurality of nozzles 32 arranged in parallel above and facing a container 33.

A first method according to the invention will now be described.

Initially, the internal fluid 36 is prepared by mixing the first phase 14 intended to form the core 17 of the drop 12 and the first precursor polymer of coacervation.

In this example, the internal fluid 36 is advantageously aqueous and the first polymer is a water-soluble polymer, for example of the anionic type.

In parallel, the external fluid 40 is also prepared by mixing an oily solvent and optionally a stabilizer for example formed by a hydrophobic resin.

The stabilizer is typically placed at the interface between the oily phase and the aqueous phase, stabilizing the drops and avoiding their coalescence before formation of the shell.

The stabilizer is for example a hydrophobic resin. This resin may for example be a silicate, such as a trimethylsiloxysilicate resin.

The mass content of stabilizer is for example comprised between 10% and 0.001%.

In this exemplary method, in FIGS. 4, 5, 6, 7 and 8, a reaction fluid 44 is also prepared. This fluid contains a second precursor polymer of coacervation, advantageously dissolved in the same oil as the one present in the external fluid 40.

The reaction fluid 44 further comprises a reaction agent capable of generating coacervation of the first polymer with the second polymer, such as an agent capable of modifying the pH like an acid or a base.

In this example, the reaction agent is a base.

Next, the internal fluid 36, the external fluid 40 and the reaction fluid 44 are respectively arranged in respective introduction means 46, 48 and 50.

Also, a liquid mass 55 formed with an oily solvent of a nature similar to the one of the external fluid 40 is introduced into the container 33.

Next, the introduction means 46, 48 and 50 are activated.

The internal fluid flow 36 circulating in the internal conduit 34 generates drops 12 of the first phase 14 at the downstream opening 52 of the internal conduit when the internal fluid 36 passes into the external fluid 40.

The drops 12 then circulate in the external fluid 40 towards the opening 54. They come into contact with the reaction fluid 44 introduced through the introduction conduit 42.

The first polymer present in the internal fluid 36 migrates to the interface between the internal fluid 36 and the external fluid 40. Also, the second polymer present in the external fluid 40 migrates to the interface between the external fluid 40 and the internal fluid 36.

Under the action of the reaction agent, coacervation between the first polymer and the second polymer occurs in order to form the shell 18.

As the first polymer and the second polymer are not initially present in the same phase, the risk that they react prematurely, notably before formation of the drops 12 of internal fluid 36 in the external fluid 40, guarantees that the shell 18 formed at the interface between the internal phase 14 and the external phase 16 is complete, very thin and does not generate total gelling of the core 17.

The thereby formed drops 12 are therefore very stable, not or not very elastic and do not tend to coalesce on each other.

At least one drop 12 formed in the external conduit 38 is then received in an outer drop 60 of external fluid 40 which is formed at the outlet of the external conduit 38, at the downstream opening 54. The outer drop 60 falls into the space 55 through an air space and the drops 12 of internal phase 14 settle in the second phase 16 formed by the external fluid 40 of the drops 60 and through the space 55.

The method according to the invention is therefore particularly effective for forming stable drops, with dimensions of more than 500 μm, without using any surfactants and in a particularly controlled way.

FIG. 5 illustrates a nozzle 32 for an alternative apparatus 30 for forming drops 12 according to the invention.

Unlike the nozzle 32 illustrated in FIG. 4, the external conduit 38 comprises an upstream segment 70 and a downstream segment 72, the upstream segment 70 partly protruding into the downstream segment 72.

The upstream segment 70 has a cross-section smaller than the cross-section of the downstream segment 72. The introduction conduit 42 opens downstream into the annular space delimited between the upstream segment 70 and the downstream segment 72.

Moreover, the contour of the cross-section of the upstream segment 70 is not necessarily homothetic to the contour of the cross-section of the downstream segment. Thus, the upstream segment 70 may have a circular cross-section and the downstream segment may have a polygonal cross-section, for example a square or rectangular cross-section.

The application of the method according to the invention in this alternative apparatus 30 is moreover similar to that of the first method.

A second method according to the invention is described with reference to FIG. 6. This method is applied batchwise in a container 20.

Initially, in step (a), a first continuous volume of internal fluid 36 is placed in the container 20. As described earlier, the internal fluid 36 contains the first phase 14 and the first polymer. Next, in step (b), a second continuous volume of external fluid 40 is introduced into the container 20 above the internal fluid 36. Both volumes are then substantially separated without being significantly dispersed into each other.

Figure 6:
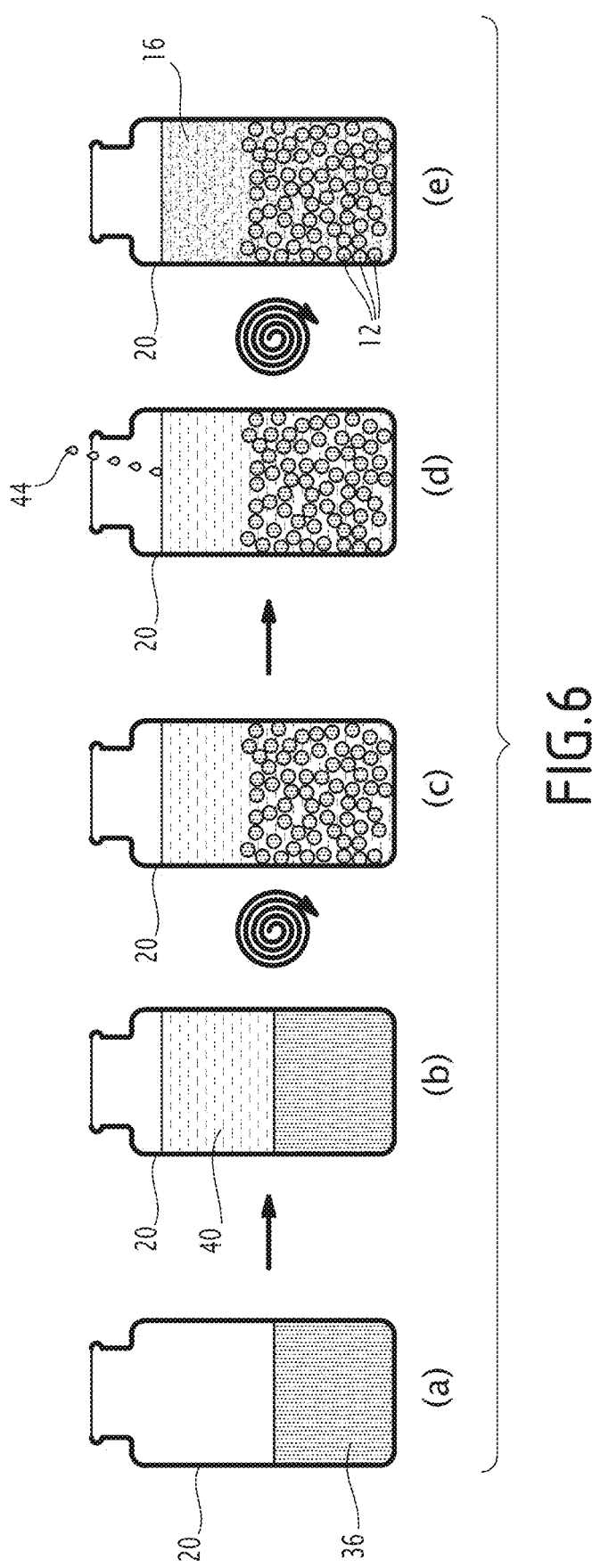
FIG. 6 is a schematic view illustrating the different steps of a second formation method according to the invention.

Next, the container 20 is stirred in order to produce a dispersion of drops 12 of internal fluid 36 in the external fluid 40 (step (c) in FIG. 6). During this step, the first precursor polymer present in the internal fluid 36 migrates to the interface between the drops 12 of the internal fluid 36 and the external fluid 40. Next, a determined amount of reaction fluid is added into the container 20 (step (d) in FIG. 6). This reaction fluid contains the reaction agent and the second precursor polymer.

Also, the second polymer present in the external phase 40 migrates to the interface between the drops 12 of internal fluid 36 and the external phase 40.

The reaction agent then migrates to the interface between the drops of internal fluid 36 and the external fluid 40 and triggers coacervation between the first polymer and the second polymer in order to form the shell 18.

In order to improve this dispersion, the container 20 is again stirred (step (e)).

As described earlier, as the first precursor polymer and the second polymer are only in contact after formation of the drops 12, or during this formation, the method avoids significant formation of gel in the drops 12 and allows formation of a shell 18 of reduced size.

As described above, the first polymer is placed in a first fluid containing the first phase 14 and the second polymer is included in a fluid immiscible with the first phase. The second polymer may be added into the second fluid in which the drops 12 are formed or in a reaction fluid optionally added after formation of the drops 12.

Examples of application of the method will now be described.

Example 1

In the experimental device of FIG. 3, a stiffening step is applied in line between a first polymer of the anionic and hydrophilic type (polyacrylic acid), and a second polymer of the cationic and lipophilic type (amodimethicone).

The first polymer is contained in the internal fluid 36 (pH comprised between 3 and 4) and the second polymer is contained in reaction fluid (which also contains a base), which is provided via a route perpendicular to the other ones, via a T connector positioned at the end of the collecting tube.

The stiffening step is based on the formation of a coacervate at the interface between the polyacrylic acid contained in the internal fluid and an amino-silicone (amodimethicone) provided by the reaction fluid, after formation of the drops.

The encounter of both these polymers causes coacervation and stiffening of the membrane around the drops.

On this described experimental device, the following flow rates are applied: FE=6,000 μL/hour, FI=4,000 μL/hour and FR=2,000 μL/hour. The composition of each fluid is described in the table below.

| Phase | Name of the product | % by mass | Function |
| --- | --- | --- | --- |
| External fluid | PDMS 6 sCt | 98% | Solvent |
| | DC 749 | 2% | Stabilizer |
| Internal fluid | Water | 99.5% | Solvent |
| | Polyacrylic acid | 0.5% | Stiffening agent |
| Reaction fluid | PDMS 6 sCt | 96% | solvent |
| | Amino-silicone | 2% | Stiffening agent |
| | Dibutylethanolamine | 2% | Base |

PDMS 6 cSt = polydimethylsiloxane (dimethicone) of viscosity 6 cSt
DC 749 = 50/50 mixture of cyclomethicone (cyclopentasiloxane) and of trimethylsiloxysilicate.

After collection, a flask is obtained containing drops with a diameter of about 900 μm having uniform size according to the method described above.

The drops are stable towards the stirring test without shearing and towards the stirring test with shearing (less than 5% of the drops are subject to coalescence). Also, no coalescence is observed after 2 weeks at 40° C.

The sample withstands a fall of one meter on a solid substrate.

The drops are non-adhesive and slip on each other when the emulsion is stirred.

Example 2

This example puts forward a stiffening step in line between a first polymer of the anionic and hydrophilic type (polyacrylic acid), and a second polymer of the cationic and lipophilic type (amodimethicone).

The manufacturing is accomplished in the same device as the one of Example 1.

The stiffening step is based on the formation of a coacervate at the interface between the polyacrylic acid contained in the internal fluid and an amino-silicone brought by the reaction fluid, after forming drops. In the described experimental device, the following flow rates are applied: FE=13,000 µl/h, FI=5,000 µl/hour and FR=1,250 µl/hour. The composition of each fluid is described in the table below.

| Phase | Name of the product | % by mass | Function |
|---|---|---|---|
| External fluid | PDMS 6 sCt | 98.5% | Solvent |
| | PEG10-dimethicone | 0.1% | Stabilizer |
| | Diethylethanolamine | 0.05% | Base |
| Internal fluid | Water | 99.5% | Solvent |
| | Polyacrylic acid | 0.5% | Stiffening agent |
| Reaction fluid | PDMS 6 sCt | 99% | Solvent |
| | Amino-silicone | 1% | Stiffening agent |

Example 3 Stiffening Device, Batchwise

This example applies a stiffening step batchwise between a first polymer of the anionic and hydrophilic type of the carbomer type (polyacrylic acid), and a second polymer of the cationic and lipophilic type (amodimethicone).

The first polymer is contained in the internal fluid (pH comprised between 3 and 4) and the second polymer is contained in the reaction fluid (which also contains a base). The composition of each fluid is described in the table below:

| Phase | Name of the product | % by mass | Function |
|---|---|---|---|
| External fluid | PDMS 6 sCt | 100% | Solvent |
| Internal fluid | Water | 99.75% | Solvent |
| | Carbomer = Polyacrylic acid | 0.25% | Stiffening agent |
| Reaction fluid | PDMS 6 sCt | 98.8% | Solvent |
| | Amino-silicone | 1% | Stiffening agent |
| | Diethylethanolamine | 0.2% | Base |

In a 4 mL glass container, 0.8 mL of internal fluid followed by 2 mL of external fluid are added. The container is then stirred for 15 s at 1,400 revolutions per minute on a vortex (IKA MS2 minishaker), whereby internal fluid drops are formed in the external fluid. In order to carry out the stiffening of the formed drops, 0.2 mL of reaction fluid are then added into the container, and the latter is then again stirred for 15 s at 1,400 revolutions per minute on a vortex (IKA MS2 minishaker). The dispersion is then left at rest for 5 minutes before being used.

At the end of this procedure, a container is obtained, containing drops of various sizes, essentially comprised between 500 µm and 1,000 µm. The drops are stable under the stirring test without shearing and under the stirring test with shearing (less than 5% of the drops are subject to coalescence). Also, no coalescence is observed after 2 weeks at 40° C.

The sample also withstands a fall from one meter on a solid substrate.

The drops are non-adhesive and slip on each other when the emulsion is stirred.

In an alternative, the first phase 14 forming drops 12 is an oily phase, and the second phase 16 in which the drops 12 are dispersed, is an aqueous phase.

The oily phase is immiscible with the aqueous phase. As described earlier, the drops 12 include a core 17 consisting of a first phase 14 and a shell for retaining and stabilizing the core 17, the shell 18 being formed with a coacervate between a first precursor polymer and a second precursor polymer as described earlier.

The drops 12 have a diameter of more than 500 micrometers and advantageously less than 3,000 micrometers, notably comprised between 800 micrometers and 2,000 microns. The shell has a thickness of less than 1,000 nanometers, notably comprised between 1 nanometer and 500 nanometers.

The precursor polymers of the coacervate are those which were described earlier.

They will not be described in more detail.

The thereby formed drops 12 are advantageously monodispersed. They have a variation coefficient, as defined above, of less than 10%.

According to the invention, the drops have a capability of deforming of more than 50%, advantageously more than 100%. This deformation capability is characterized by the gamma coefficient calculated through the equation:

$$\gamma = \frac{A_{MAX} - A_{INIT}}{A_{MAX}},$$

wherein $A_{MAX}$ is the apparent area of the drop 12 just before its breaking, and $A_{INIT}$ is the initially measured apparent area of the drop 12.

In order to characterize the deformability of the drops 12, the following procedure is applied. An optical table of the «THORLABS» type is used as a support for the experimental measurement device for isolating as much as possible the vibrations of this experimental device. A glass plate is maintained horizontally with clamps at about 10 centimeters above the optical table. A circular spirit level is used for checking horizontality. An elevator is placed under the glass plate while being stationary by means of «THORLABS» clamps. A sheet of white paper is assembled on the elevator or a white adhesive tape on the glass plate in order to have better contrast. A microscope slide is placed on the elevator and is displaceable towards the glass plate.

A camera Veo Discovery VMS 001 connected to a computer films the experimental device from the top. The acquisition software package used is Astra Image Webcam Video Graveur. The recorded videos are then utilized with the software package Image J. The distances in pixels are converted into millimeters by means of a standard of known size (for example a glass marble, the specific size of which being measured with a microscope with a micrometer gauge).

Initially, the glass plate and the slide are separated by a few centimeters.

A single drop 12 isolated from the dispersion 10 according to the invention, surrounded with a little second phase 16 is laid on the slide. The slide is then brought closer to the plate. When the second phase 16 begins to wet the plate, the slide is slightly moved down in order to obtain a drop 12 with as little stress as possible. A measurement is taken in order to determine the initial apparent area $A_{INIT}$ of the drop 12.

Next, the drop 12 is compressed until it bursts, for example at a rate for bringing the slide closer to the plate, substantially equal to 0.5 mm/min. Just before bursting of the drop 12, for example 50 microseconds before the bursting of the drop 12, the maximum apparent area $A_{MAX}$ of the drop 12 is measured.

The experiment is then reproduced for a number of drops 12 of more than 10 and for example equal to 14. Monodispersity of the drops 12 is checked so that it is less than 10%.

Figure 7:
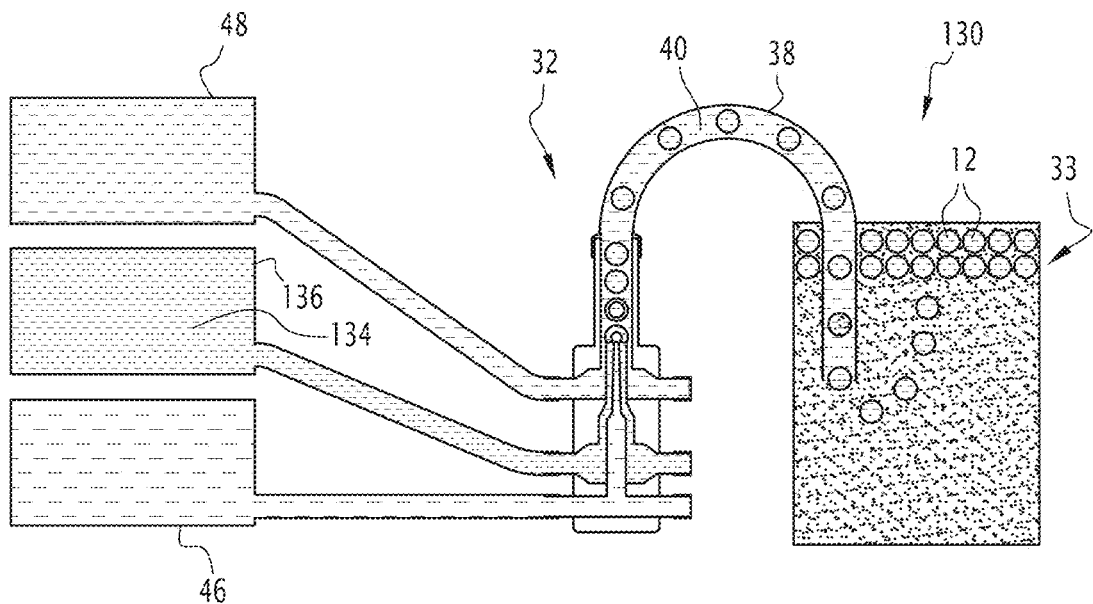
FIG. 7 is a view similar to FIG. 3 of an alternative application apparatus.
Figure 8:
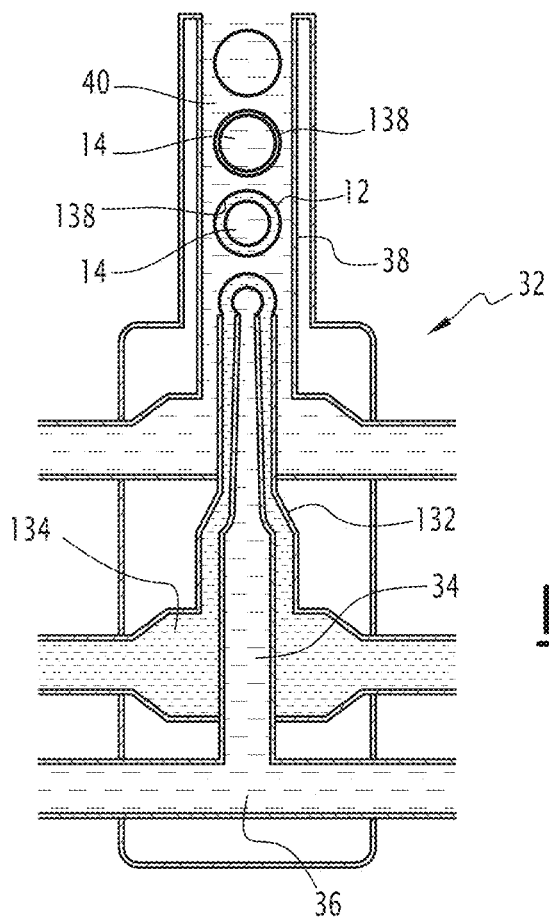
FIG. 8 is an enlarged view of the nozzle for forming drops of FIG. 7.

An alternative of the method for forming the drops 12 of the dispersion 10 may be applied in an apparatus 130 illustrated in FIGS. 7 and 8.

As illustrated by these figures, the apparatus 130 includes at least one nozzle 32 for forming the drops 12 and a container 33 for receiving the formed drops 12.

Unlike the apparatus 30 illustrated in FIGS. 3 and 4, the internal conduit 34 for introducing internal fluid 36 opens into an intermediate conduit 132 for introducing an intermediate fluid 134. The intermediate fluid 134 is miscible with the internal fluid 36 comprising the first phase 14. The intermediate conduit 132 opens into the external conduit 38.

The external conduit 38 opens into the container 33 while being advantageously immersed in the volume of fluid 35.

In the example illustrated in FIG. 7, the external conduit 38 is bent and substantially has the shape of a crook opening into the container 33.

In this example, the internal conduit 34 and the intermediate conduit 132 open upwards into a vertical upward segment of the external conduit 38. The external conduit 38 opens downward into the container 33.

In addition to the means 46 for introducing internal fluid into the internal conduit 36 and in addition to the means 48 for introducing external fluid into the external conduit 38, the apparatus 130 includes means 136 for introducing intermediate fluid 134 into the intermediate conduit 132.

Advantageously, the apparatus 130 includes a plurality of parallel nozzles 32 connected to common introduction means 46, 48, 136. Such an apparatus is for example described in French application No. 11 55455 of the Applicant.

In this example, the first phase 14 is oily. For example it is formed on the basis of an oil as described above. It advantageously includes molecules of cosmetic interest, such as cosmetic actives.

The intermediate fluid 134 is miscible with the internal fluid 36. It for example consists of an oily phase identical to the first phase 14 or miscible with the first phase 14.

The intermediate fluid 134 for example consists of at least one oil selected from the group comprising silicone oils, mineral oils, vegetable oils, fatty acid and/or fatty alcohol esters, typically $C_1$-$C_{20}$ esters, and oils compatible with the esters such as apolar solvents.

As this will be seen below, the intermediate fluid 134 is intended to form a film 138 around the drop 12 formed at the outlet of the intermediate conduit 132 in the external fluid 40. Thus, the intermediate fluid 134 delays diffusion of the first precursor polymer of the coacervate present in the internal fluid 36 until the intermediate fluid 138 has mixed with the internal fluid 36.

In this example, the first precursor polymer of the coacervate present in the first fluid 36 is lipophilic. It is advantageously of the cationic and lipophilic type. It may for example be formed with a polymer derived from silicone such as amodimethicone.

The external fluid 40 is aqueous. The second precursor polymer of the coacervate introduced into the external fluid 40 is hydrophilic. It is advantageously of the anionic type. For example it is formed with a polyacrylic acid.

Advantageously, the internal phase 36 includes between 0.05% by mass and 10% by mass of the first precursor polymer of the coacervate, based on the total mass of the intermediate fluid 36.

Also, the external fluid 40 includes between 0.05% by mass and 10% by mass of the second precursor polymer of the coacervate, based on the total mass of the external fluid 40.

A method for forming a dispersion 10 of drops 12 applied in the apparatus 130 will now be described.

Initially, the internal fluid 36 is prepared by mixing the first phase 14 intended to form the core 17 of the drop 12 and the first precursor polymer of the coacervate.

In parallel, the external fluid 40 is prepared by mixing a solvent intended to form the second phase 16 and a second precursor polymer of the coacervate.

Next, the internal fluid 36, the external fluid 40 and the intermediate fluid 136 are placed in the respective introduction means 46, 136, 48. Next, the introduction means 46, 48 and 136 are activated.

The internal fluid flow 36 circulating in the internal conduit 34 opens into the intermediate conduit 132 so as to be surrounded by a film 138 of intermediate fluid 134.

Next, at the end of the intermediate conduit 132, drops 12 of internal fluid 36 totally surrounded by a film 138 of intermediate fluid 134 are formed. The drops 12 then circulate in the external fluid 40 within the external conduit 38.

The film 138 at least partly delays the diffusion of the first precursor polymer of the coacervate towards the interface between the drop 12 and the external fluid 40.

Next, the intermediate fluid 134 is gradually mixed with the internal fluid 36, allowing migration of the first precursor polymer of the coacervate as far as the interface between the drop 12 and the external fluid 40.

The second polymer present in the external fluid 40 also migrates to this interface.

The coacervation between the first polymer and the second polymer then occurs at the interface in order to form the shell 18. The shell 18 formed at this interface is therefore complete, very thin and does not generate total gelling of the core 17.

The thereby formed drops 12 are therefore very stable, not or not very elastic, and do not tend to coalesce with each other. The drops 12 then move upwards in the container 33 towards the surface and come into contact with each other, without any coalescence at least for three months at room temperature and at 50° C.

When the second polymer is acrylic acid, it is advantageously maintained in acid form, in order to maintain low viscosity of the external phase 16, notably lower than 500 mPa·s.

This allows creaming of the drops 12 towards the top of the container 33.

In an alternative, the composition of the second phase 16 is modified, by adding a solution miscible with this phase 16 or as partial replacement for the phase 16.

An exemplary application of this method will now be described.

Example 4

In the experimental device of FIGS. 6 and 7, a stiffening step is applied between a first coacervate precursor polymer of the cationic and lipophilic type (amodimethicone), and a second coacervate precursor polymer of the anionic and hydrophilic type (polyacrylic acid).

The first polymer is contained in the oily internal fluid 36. The second polymer is contained in the aqueous external fluid 40.

The stiffening step is based on the formation of a coacervate at the interface between the polyacrylic acid contained in the external fluid 40 and an amino silicone (amodimethicone) contained in the internal fluid 36, after formation of drops 12 in the external fluid 40.

The encounter of both these polymers causes coacervation and stiffening of the membrane around the drops 12. In the apparatus 130 described in FIG. 7, the following flow rates are applied:

External fluid: 80 mL/hour;
Internal fluid: 15 mL/hour;
Intermediate fluid: 5 mL/hour.

The composition of each fluid is described in the table below.

| Phase | Name of the product | % by mass | Function |
|---|---|---|---|
| Internal fluid | PDMS 6 sCt | 99.5% | Solvent |
| | Amino-silicone | 0.5% | Coacervation agent |
| External fluid | Water | 99.5% | Solvent |
| | Polyacrylic acid | 0.5% | Coacervation agent |
| Intermediate fluid | PDMS 6 sCt | 100% | Solvent |

As a result of the collection, a container 33 is obtained, containing drops with a diameter of about one millimeter with a coacervate membrane.

These drops have a deformation before breaking characterized by the aforementioned gamma coefficient equal to 222.37% with a variance coefficient of 9.49%.

The thereby formed dispersion 10 comprises 20% by volume of drops 12.

In an alternative, the dispersions 10 discussed earlier with reference of FIGS. 1 and 7 contain a perfuming agent.

Among the perfuming agents, mention may notably be made of any type of perfume or fragrance, these terms being equally used here. These perfumes or fragrances are well known to one skilled in the art and notably include those mentioned for example in S. Arctander, Perfume and Flavor Chemicals (Montclair, N.J., 1969), S. Arctander, Perfume and Flavor Materials of Natural Origin (Elizabeth, N.J., 1960) and in "Flavor and Fragrance Materials", 1991 (Allured Publishing Co. Wheaton, Ill. USA).

The perfumes used within the scope of the present invention may comprise natural products such as extracts, essential oils, absolutes, resinoids, resins, solid perfumes, etc . . . as well as basic synthesis substances such as hydrocarbons, alcohols, aldehydes, ketones, ethers, acids, esters, acetals, ketals, nitriles, etc . . . , including saturated and unsaturated compounds, aliphatic, alicyclic and heterocyclic compounds.

Advantageously, the dispersion 10 according to the invention is without any alcohol.

Within the scope of the present description, by «alcohol» is meant a linear or branched hydrocarbon compound comprising from 1 to 4 carbon atoms, in which at least one hydrogen atom is replaced with a hydroxyl function. Such an alcohol is typically ethanol, isopropanol, n-butanol or any other usual alcohol in the field of cosmetics.

Advantageously, the first phase 14 and the second phase 16 according to the invention comprise a reduced amount of surfactant, generally tolerated within the scope of a cosmetic application. Preferably, the dispersion 10 is totally free of surfactant.

The drops 12 are formed by a method as described above.

When the second phase 16 is oily and when the first phase 14 is aqueous, the method is applied by placing the perfuming agent in a fluid intended to form the second phase 16, advantageously in the external fluid 40 intended to receive the drops 12 of internal fluid 36.

Alternatively, the drops 12 of the dispersion 10 according to the invention are formed in a second oily phase 16 without any perfuming agent. Next, a portion of the second oily phase 16 is extracted out of the container for collecting the dispersion 10. This extracted portion is replaced with a perfuming agent. The dispersion then includes more than 30% by mass, advantageously more than 35% by mass of drops 12 and more than 10% by mass, advantageously more than 30% by mass of perfuming agent based on the total mass of the dispersion 10.

Example 5

This example applies the manufacturing of a dispersion containing a perfuming agent. The stiffening step is based on the formation of a coacervate at the interface between the polyacrylic acid contained in the internal fluid 36 and an amino silicone contained in the reaction fluid 44 after forming the drops 12. The following flow rates are applied:

Internal fluid: 40 mL/hour;
External fluid: 100 mL/hour;
Reaction fluid: 10 mL/hour.

The composition of each fluid is described in the table below:

| Phase | Name of the product | % by mass | Function |
|---|---|---|---|
| Internal fluid | Water | 99.5% | Solvent |
| | Polyacrylic acid | 0.5% | Coacervation agent |
| External fluid | Isononyl Isononoate | 33% | Solvent |
| | Perfume | 66% | Perfume |
| Reaction fluid | Diethylethanolamine | 0.5% | Base |
| | Amino-silicone | 1% | Coacervation agent |
| | Isononyl Isononoate | 98.5% | Solvent |

With this method it is possible to obtain a dispersion 10 of monodispersed drops 12 with a diameter equal to 1 mm.

In an alternative, the dispersion 10 includes drops 12 of a first oily phase 14 dispersed in a second aqueous phase 16. The perfuming agent is placed in the drops 12 of the first phase 14. In this case, the internal fluid 36 is oily and contains the perfuming agent, in addition to the first coacervation precursor polymer. The intermediate phase 134 is miscible with the internal fluid 36.

The external fluid 40 is aqueous. It contains the second coacervation precursor polymer. Optionally, other molecules, notably cosmetic actives, may be added into the external fluid 40.

The mass content of perfuming agent in the internal fluid 36, based on the total mass of the internal fluid 36, is more than 40% by mass and is notably comprised between 50% by mass and 70% by mass.

Examples for making dispersions 10 containing drops 12 of an oily phase, provided with a perfuming agent, dispersed in a second aqueous phase 16 will now be described.

Example 6

This example applies to the making of a dispersion containing a perfuming agent. This making is carried out in an apparatus 130 as illustrated in FIGS. 7 and 8.

The stiffening step is based on the formation of a coacervate at the interface between the polyacrylic acid contained in the external fluid 40, and an amino silicone contained in the internal fluid 36 after forming drops, and after mixing between the intermediate fluid 134 of the film 138 and the internal fluid 36. In the described apparatus 130, the following flow rates are applied:
- internal fluid: 15 mL/hour;
- external fluid: 80 mL/hour;
- intermediate fluid: 5 mL/hour.

The composition of each fluid is described in the table below:

| Phase | Name of the product | % by mass | Function |
|---|---|---|---|
| Internal fluid | Isononyl Isononoate | 33% | Solvent |
| | Perfume | 66% | |
| | Amino-silicone | 1% | Coacervation agent |
| External fluid | Water | 99.5% | Solvent |
| | Polyacrylic acid | 0.5% | Coacervation agent |
| Intermediate fluid | Isononyl Isononoate | 100% | Solvent |

A dispersion 10 of drops 12 of a first oily phase 14 containing a perfuming agent dispersed in a second aqueous phase 16 is obtained. The drops 12 are monodispersed, have a diameter of 1 millimeter and a coacervate shell 18.

The mass content of the drops in the dispersion 10 is 20% by mass and the mass content of perfume in the dispersion is of 10% by mass, based on the total mass of the dispersion.

Example 7

A method similar to the one of Example 6 is applied. However, unlike the method described in Example 6, a portion of the second phase 16 obtained at the end of the production of drops 12 (for example after one hour) is removed and replaced with a 0.4% triethanolamine solution. This solution is capable of gelling the polyacrylic acid present in the aqueous phase. The dispersion then includes 40% by mass of drops 12 and 20% by mass of perfuming agent.

Example 8

This example is identical to Example 7, except that the apparatus 130 is configured for forming drops 12 with a diameter of 2 millimeters. The final dispersion 10 then includes 40% by mass of drops with a diameter of 2 millimeters and 20% by mass of perfume.

Example 9

This example is identical to Example 6, except that at the end of the production of drops 12 (for example after one hour), a portion of the second phase 16 is removed and replaced with a cosmetic composition described in the table below:

| Phase | Name of the product | % by mass |
|---|---|---|
| A | Water | 87.050% |
| A | Polyacrylic acid | 0.150% |
| B | Glycerol | 5.000% |
| B | Propylene glycol | 5.000% |
| B | Xanthan gum | 0.250% |
| C | Water | 2.000% |
| C | Chlorphenesin (3-(4-chlorophenoxy)-1,2-propanediol) | 0.300% |
| C | Phenoxyethanol | 0.250% |

The phases A, B and C are prepared separately. Phase B is then added to phase A, and then once the solution is homogeneous, phase C is added into the mixture.

Once the cosmetic composition is mixed with the dispersion, a 1.3% triethanolamine solution (10 mL) is added into the second phase 16 in order to gel the polyacrylic acid. This dispersion then includes 10% by mass of the drops and 5% by mass of perfume.

Example 10

This example is identical to Example 6. However, unlike Example 6, at the end of the production of drops 12 (for example after one hour), a portion of the second phase 16 is removed and replaced with water. This reduces the concentration of polyacrylic acid in the second phase 16. After homogenization, a portion of the second phase 16 is again removed and a 0.23% triethanolamine solution is added. The obtained dispersion then includes 20% by mass of drops 12 and 10% by mass of perfume.

The final mass content of polyacrylic acid in the second phase 16 is less than 1% and is notably 0.073% in the second phase 16. This leads to acceptable viscosity so that the dispersion 10 may be sprayed.

More generally, by means of the invention which has just been described, it is possible to obtain a perfuming cosmetic composition comprising the dispersion according to the invention. This perfuming cosmetic composition has the following advantages.

Firstly, it is not necessary to use an alcohol, notably ethanol, for preparing the dispersion 10 according to the invention. Indeed, as the dispersion 10 is biphasic, it is possible to disperse the perfuming agent in a small amount of oily phase.

The dispersion according to the invention is particularly stable. The drops 12 provided with a coacervate shell 18, block coalescence phenomena which gives the possibility of maintaining the integrity of the dispersion 10.

The dispersion 10 is further easily sprayable. The viscosity of the phases 14, 16 is sufficiently low to allow such spraying and the coacervate shell 18 has mechanical strength such that it is destroyed by passing into a spraying device.

Further, the drops 12 are non-adhesive, as discussed above. The formation of the coacervate shell 18 therefore does not require the use of a surfactant which in certain cases produces an adhesive effect in the formulation of perfumes without alcohol of the nano- or micro-emulsion type.

The dispersion 10 according to the invention may comprise high perfuming agent loading levels, for example of more than 10% by mass, notably more than 20% by mass and which may attain 40% by mass. This may easily be attained and in the absence of alcohol in the dispersion 10.

In an alternative, agents for modifying the olfactory profile, for example for increasing the remanence of the perfume, are added in the first phase 14 and/or in the second phase 16.

These agents for modifying the olfactory profile are for example lipophilic copolymers of esters or Guerbet alcohols.

In an alternative, a xanthan solution is added in the second phase 16 for modifying the properties of the final gel, after gelling the phase 16.

In still another alternative, it is possible to recover the drops 12 of the first phase 14 and to disperse them again in a new second phase 16.

The invention claimed is:

1. A dispersion of drops of a first phase in a second phase, the solubility of the first phase in the second phase being less than 5% by mass, each drop including a core formed with the first phase and a shell formed with a coacervate layer interposed between the first phase and the second phase,
wherein the coacervate layer comprises a first precursor polymer of the coacervate and a second precursor polymer of the coacervate, one of the first phase and of the second phase being aqueous, and the other of the first phase and of the second phase being oily,
wherein one of the first precursor and of the second precursor comprises a lipophilic polymer that is capable of being ionized upon contact with an aqueous phase, and
wherein the other of the first precursor polymer and of the second precursor polymer comprises a hydrophilic polymer capable of being ionized.

2. The dispersion according to claim 1, wherein the drops have diameter of more than 500 micrometers and less than 3,000 microns.

3. The dispersion according to claim 1, wherein the shell has a thickness of less than 1,000 nanometers.

4. The dispersion according to claim 1, wherein the first precursor polymer of the coacervate is a first polymer which may be ionized in order to have a first charge, and the second precursor polymer of the coacervate is a second polymer which may be ionized in order to have a second charge opposite to the first charge.

5. The dispersion according to claim 1, wherein a perfuming agent is placed in one of the first phase and the second phase.

6. The dispersion according to claim 1, wherein each drop of the first phase has a deformation before breaking of more than 50%, the deformation before breaking being characterized by the gamma coefficient calculated through the equation:

$$\gamma = \frac{A_{MAX} - A_{INIT}}{A_{MAX}},$$

$A_{MAX}$ being the apparent area of the drop just before its breaking and $A_{INIT}$ being the initially measured apparent area of the drop.

7. The dispersion according to claim 1, wherein the mass content of drops of the first phase in the dispersion is comprised between 0.1% by mass and 70% by mass.

8. A cosmetic composition comprising the dispersion according to claim 1.

9. The dispersion according to claim 1, wherein the drops have a diameter of between 800 microns and 2,000 microns.

10. The dispersion according to claim 1, wherein the shell has a thickness of between 1 nanometer and 500 nanometers.

11. The dispersion according to claim 1, wherein a perfuming agent is placed in the oily phase.

12. The dispersion according to claim 1, wherein each drop of the first phase has a deformation before breaking of more than 100%, the deformation before breaking being characterized by the gamma coefficient calculated through the equation:

$$\gamma = \frac{A_{MAX} - A_{INIT}}{A_{MAX}},$$

$A_{MAX}$ being the apparent area of the drop just before its breaking and $A_{INIT}$ being the initially measured apparent area of the drop.

13. The dispersion according to claim 1, wherein the mass content of drops of first phase in the dispersion is comprised between 3% by mass and 50% by mass.

14. The dispersion according to claim 6, wherein each drop of the first phase has a deformation before breaking of more than 50%, the deformation before breaking being characterized by the gamma coefficient calculated through the equation:

$$\gamma = \frac{A_{MAX} - A_{INIT}}{A_{MAX}},$$

$A_{MAX}$ being the apparent area of the drop 50 microseconds before the breaking of the drop and $A_{INIT}$ being the initially measured apparent area of the drop.

15. The dispersion according to claim 12, wherein each drop of the first phase has a deformation before breaking of more than 100%, the deformation before breaking being characterized by the gamma coefficient calculated through the equation $$\gamma = \frac{A_{MAX} - A_{INIT}}{A_{MAX}},$$

$A_{MAX}$ being the apparent area of the drop 50 microseconds before the breaking of the drop and $A_{INIT}$ being the initially measured apparent area of the drop.

16. The dispersion according to claim 1, wherein the lipophilic polymer which may be ionized in contact with an aqueous phase is a polymer containing a silicone and containing a functional group which may be ionized.

17. The dispersion according to claim 1, wherein each drop comprises, by mass based on the mass of the drop:
from 0.05% to 10% of a polymer P1 of the anionic and hydrophilic type, and
from 0.05% to 10% of a polymer P2 of the cationic and lipophilic type.

18. The dispersion according to claim 1, wherein each drop comprises, by mass based on the mass of the drop:
from 0.05% to 10% of a polymer P1 of the cationic and hydrophilic type, and
from 0.05% to 10% of a polymer P2 of the anionic and lipophilic type.

* * * * *